(12) United States Patent
Hicke et al.

(10) Patent No.: US 6,596,491 B2
(45) Date of Patent: Jul. 22, 2003

(54) TENASCIN-C NUCLEIC ACID LIGANDS

(75) Inventors: Brian Hicke, Boulder, CO (US);
Stephen Warren, Boulder, CO (US);
David Parma, Boulder, CO (US);
Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/854,662

(22) Filed: May 14, 2001

(65) Prior Publication Data

US 2003/0104377 A1 Jun. 5, 2003

Related U.S. Application Data

(60) Division of application No. 09/364,902, filed on Jul. 29, 1999, now Pat. No. 6,232,071, which is a continuation-in-part of application No. 08/434,425, filed on May 3, 1995, now Pat. No. 5,789,157, which is a continuation-in-part of application No. 07/714,131, filed on Jun. 10, 1991, now Pat. No. 5,475,096, which is a continuation-in-part of application No. 07/536,428, filed on Jun. 11, 1990, now abandoned, and a continuation-in-part of application No. 07/964,624, filed on Oct. 21, 1992, now Pat. No. 5,496,938, application No. 09/854,662, which is a continuation-in-part of application No. 08/993,765, filed on Dec. 18, 1997.

(51) Int. Cl.[7] .................................................. C12Q 1/68
(52) U.S. Cl. ...................... 435/6; 435/91.2; 530/350; 530/387.1; 536/221.1; 536/24.2; 536/25.4
(58) Field of Search .................. 435/6, 91, 2; 530/350, 530/387.1; 536/22.1, 25.4, 24.2

(56) References Cited

U.S. PATENT DOCUMENTS

| | | | |
|---|---|---|---|
| 5,436,132 A | * | 7/1995 | Kimura et al. |
| 5,475,096 A | | 12/1995 | Gold |
| 5,582,981 A | * | 12/1996 | Toole et al. |
| 5,723,323 A | | 3/1998 | Kauffman et al. |
| 5,789,157 A | * | 8/1998 | Jensen et al. |
| 5,859,228 A | | 1/1999 | Janjic et al. |
| 6,127,119 A | * | 10/2000 | Stephens et al. |
| 6,242,246 B1 | * | 6/2001 | Gold et al. |

FOREIGN PATENT DOCUMENTS

| | | |
|---|---|---|
| GB | 2 183 661 A | 6/1987 |
| WO | WO 89/06694 | 7/1989 |
| WO | WO 91/19813 | 12/1991 |
| WO | WO 92/14843 | 9/1992 |

OTHER PUBLICATIONS

Bigner et al. (1998) Journal of Clinical Oncology 16:2202.
Ellington & Szostak (1990) Abstracts of papers presented at the 1990 meeting on RNA Processing, Cold Spring Harbor Laboratory, Cold Spring Harbor, NY, p. 84.
Joyce & Inoue (1989) Nucleic Acids Research 17:711.
Joyce (1989) Gene 82:83.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Merlo et al. (1997) Int. J. Cancer 71:810.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Paganelli et al. (1999) Eur. J. Nucl. Med. 26:348.
Paganelli et al. (1994) Eur. J. Nucl. Med. 21:314.
Robertson & Joyce (1990) Nature 344:467.
Szostak, "Structure and Activity of Ribozymes," in *Redesigning the Molecules of Life*, (S.A. Benner, ed.) Springer–Verlag Berline Heidelberg, pp. 87–113, (1988).
Thiesen & Bach (1990) Nucleic Acids Research 18:3203.

* cited by examiner

*Primary Examiner*—Stephanie Zitomer
(74) *Attorney, Agent, or Firm*—Swanson & Bratschun, LLC

(57) ABSTRACT

Methods are described for the identification and preparation of nucleic acid ligands to tenascin-C. Included in the invention are specific RNA ligands to tenascin-C identified by the SELEX method. Further included in the invention are methods for detecting the presence of a disease condition in a biological tissue in which tenascin-C is expressed.

18 Claims, 5 Drawing Sheets

SEQUENCE LISTING

<160> NUMBER OF SEQ ID NOS: 65

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: N at positions 17-56 is A, C, G or T.

<400> SEQUENCE: 1
tcgcgcgagt cgtctgnnnn nnnnnnnnnn nnnnnnnnnn nnnnnnccgc      60
atcgtcctcc c                                                71

```
<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
taatacgact cactataggg aggacgatgc gg                                   32

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
tcgcgcgagt cgtctg                                                    16

<210> SEQ ID NO 4
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 4
gggaggacga ugcggcaauc aaaacucacg uuauuccuc aucuauuagc uuccccagac     60
gacucgcccg a                                                         71

<210> SEQ ID NO 5
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 5
gggaggacga ugcggcaauc uccgaaaaag acucuuccug cauccucuca cccccagac     60 gacucgcccg a                                                         71

<210> SEQ ID NO 6
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 6
gggaggacga ugcggcaacc ucgaaagacu uuucccgcau cacuguguac uccccagac     60 gacucgcccg a                                                         71
```

<210> SEQ ID NO 7
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 7
gggaggacga ugcggcaacc ucgauagacu uucccgcau cacuguguac uccccccagac    60 gacucgcccg a    71

<210> SEQ ID NO 8
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 8
gggaggacga ugcggcaacc ucaaucuuga cauuucccgc accuaaauuu gcccccagac    60
gacucgcccg a    71

<210> SEQ ID NO 9
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 9
gggaggacga ugcggcaaac gaucacuuac cuuuccugca ucugcuagcc uccccccagac    60 gacucgcccg a    71

<210> SEQ ID NO 10
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 10
gggaggacga ugcggacgcc agccauugac ccucgcuucc acuauuccau cccccagac    60 gacucgcccg a    71

<210> SEQ ID NO 11
<211> LENGTH: 70
<212> TYPE: RNA
<213> ORGANISM: Artificial Sequence
<220> FEATURE:
<223> OTHER INFORMATION: Description of Artificial Sequence: Synthetic

```
                      Sequence
<221> NAME/KEY: modified_base
<222> LOCATION: (1)..(70)
<223> OTHER INFORMATION: All pyrimidines are 2'F.

<400> SEQUENCE: 11
gggaggacga ugcggccaac cucauuuuga cacuucgccg caccuaauug cccccagacg       60
acucgcccga                                                             70

<210> SEQ ID NO 12
<211> LENGTH: 15
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(15)
<223> OTHER INFORMATION: All pyrimidines are 2'F; n at positions 4 and
      10 is A, C, G or U.

<400> SEQUENCE: 12
gacnyuuccn gcayc                                                       15

<210> SEQ ID NO 13
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 13
gggaggacga ugcggaaccc auaacgcgaa ccgaccaaca ugccucccgu gccccagac       60 gacucgcccg a                                                           71

<210> SEQ ID NO 14
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 14
gggaggacga ugcggugccc auagaagcgu gccgcuaaug cuaacgcccu cccccagacg      60
acucgcccga                                                             70

<210> SEQ ID NO 15
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 15
gggaggacga ugcggugccc acuaugcgug ccgaaaaaca uuuccccuc uacccagac        60
```
gacucgcccg a                                                          71

<210> SEQ ID NO 16
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 16
gggaggacga ugcggaacac uuucccaugc gucgccauac cggauauauu gcucccagac      60
gacucgcccg a                                                          71

<210> SEQ ID NO 17
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 17
gggaggacga ugcggacugg accaaaccgu cgccgauacc cggauacuuu gcucccagac      60
gacucgcccg a                                                          71

<210> SEQ ID NO 18
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 18
gggaggacga ugcggaacaa ugcacucguc gccguaaugg auguuuugcu cccugcagac      60
gacucgcccg a                                                          71

<210> SEQ ID NO 19
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 19
gggaggacga ugcgguuaag ucucgguuga augcccaucc cagaucccccc ugacccagac    60 gacucgcccg a                                                          71

<210> SEQ ID NO 20
<211> LENGTH: 71
<212> TYPE: RNA

```
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 20
gggaggacga ugcggauggc aagucgaacc auccccacg cuucuccugu uccccagac      60 gacucgcccg a                                                         71

<210> SEQ ID NO 21
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 21
gggaggacga ugcgggaagu uuucucugcc uugguuucga uuggcgccuc cccccagac     60 gacucgcccg a                                                         71

<210> SEQ ID NO 22
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 22
gggaggacga ugcggucgag cggucgaccg ucaacaagaa uaaagcgugu cccugcagac    60
gacucgcccg a                                                         71

<210> SEQ ID NO 23
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 23
gggaggacga ugcggauggc aagucgaacc auccccacg cuucuccugu uccccagac      60 gacucgcccg a                                                         71

<210> SEQ ID NO 24
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(76)
<223> OTHER INFORMATION: All pyrimidines are 2'F.
```

<400> SEQUENCE: 24
gggaggacga ugcggacuag accgcgaguc cauucaacuu gcccaaaaaa aaaccucccc    60
cagacgacuc gcccga    76

<210> SEQ ID NO 25
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 25
gggaggacga ugcgggagau caacauuccu cuaguuuggu uccaaccuac accccagac    60 gacucgcccg a    71

<210> SEQ ID NO 26
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 26
gggaggacga ugcggacgag cgucucauga ucacacuauu ucgucucagu gugcacagac    60
gacucgcccg a    71

<210> SEQ ID NO 27
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 27
gggaggacga ugcggucgac cucgaaugac ucuccaccua ucuaacaucc cccccagac    60 gacucgcccg a    71

<210> SEQ ID NO 28
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 28
gggaggacga ugcggucgac cucgaaugac ucuccaccua ucuaacagcc uuccccagac    60
gacucgcccg a    71

<210> SEQ ID NO 29
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 29
gggaggacga ugcggagaac ucauccuaac cgcucuaaca aaucuuglcc gaccgcagac    60 gacucgcccg a                                                        71

<210> SEQ ID NO 30
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 30
gggaggacga ugcggauaau ucgacaccaa ccagglcccg gaaaucaucc cucugcagac    60
gacucgcccg a                                                        71

<210> SEQ ID NO 31
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 31
gggaggacga ugcggaaacc aaccguugac caccuuuucg uuccggaaa gucccagac     60 gacucgcccg a                                                        71

<210> SEQ ID NO 32
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 32
gggaggacga ugcggaagcc aacccucuag ucagccuuuc guuucccacg ccacccagac   60
gacucgcccg a                                                        71

<210> SEQ ID NO 33
<211> LENGTH: 72
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(72)
<223> OTHER INFORMATION: All pyrimidines are 2'F.

<400> SEQUENCE: 33
gggaggacga ugcgggacca acuaaacugu ucgaaagcug gaacaugucc ugacgccaga    60
cgacucgccc ga                                                       72

<210> SEQ ID NO 34
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 34
gggaggacga ugcggaccaa cuaaacuguu cgaaagcugg aacacguccu gacgccagac    60
gacucgcccg a                                                        71

<210> SEQ ID NO 35
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 35
gggaggacga ugcggaccaa cuaaacuguu cgaaagcuag aacacgucca gacgccagac    60
gacucgcccg a                                                        71

<210> SEQ ID NO 36
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 36
gggaggacga ugcggaccaa cuaaacuguu cgaaagcugg aacacguucu gacgccagac    60
gacucgcccg a                                                        71

<210> SEQ ID NO 37
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 37

-continued gggaggacga ugcggaccaa cuaaacuguu cgaaagcugg aauacguccu gacgccagac    60
gacucgcccg a    71

<210> SEQ ID NO 38
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 38
gggaggacga ugcggaaguu uagugcucca guuccgacac uccucuacuc agccccagac    60
gacucgcccg a    71

<210> SEQ ID NO 39
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 39
gggaggacga ugcggagcca gagccucucu caguucuaca gaacuuaccc acuggcagac    60
gacucgcccg a    71

<210> SEQ ID NO 40
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 40
gggaggacga ugcggaccua acucaaucag gaaccaaacc uagcacucuc auggccagac    60
gacucgcccg a    71

<210> SEQ ID NO 41
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 41
gggaggacga ugcgggagau caacauuccu cuaguuuggu uccaaccuac accccagac    60 gacucgcccg a    71

<210> SEQ ID NO 42
<211> LENGTH: 71

<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 42
gggaggacga ugcggaucuc gauccuucag cacuucauuu cauuccuuuc ugccccagac    60
gacucgcccg a                                                         71

<210> SEQ ID NO 43
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 43
gggaggacga ugcggacgau ccuuccuua acauuucauc auuucucuug ugccccagac    60
gacucgcccg a                                                         71

<210> SEQ ID NO 44
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 44
gggaggacga ugcggugacg acaacucgac ugcauaucuc acaacuccug ugccccagac    60
gacucgcccg a                                                         71

<210> SEQ ID NO 45
<211> LENGTH: 72
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(72)
<223> OTHER INFORMATION: All pyrimidines are 2'F.

<400> SEQUENCE: 45
gggaggacga ugcggacuag accgcguaguc cauucaacuu gcccaaaaac cucccccaga    60
cgacucgccc ga                                                        72

<210> SEQ ID NO 46
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)

<223> OTHER INFORMATION: All pyrimidines are 2'F.

<400> SEQUENCE: 46
gggaggacga ugcgggcgca ucgagcaaca uccgauucgg auuccuccac uccccagac    60 gacugcccga                                                         70

<210> SEQ ID NO 47
<211> LENGTH: 50
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(50)
<223> OTHER INFORMATION: All pyrimidines are 2'F; linkage at positions
      50 and 51 is 3'-3'.

<400> SEQUENCE: 47
gggaggacga ugcggaacaa ugcacucguc gccguaaugg auguuuugcu              50

<210> SEQ ID NO 48
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; linkage at positions
      55 and 56 is 3'-3'.

<400> SEQUENCE: 48
gggaggacga ugcggaacaa ugcacucguc gccguaaugg auguuuugcu cccug        55

<210> SEQ ID NO 49
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5 and 55 are 2'OMe; a at position 4 is 2'OMe; linkage at positions
      55 and 56 is 3'-3'.

<400> SEQUENCE: 49
gggaggacga ugcggaacaa ugcacucguc gccguaaugg auguuuugcu cccug        55

<210> SEQ ID NO 50
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 6, 9,
      12 and 14 are 2'OMe; a's at positions 7 and 10 are 2'OMe; linkage
      at positions is 3'-3'.

<400> SEQUENCE: 50
gggaggacga ugcggaacaa ugcacucguc gccguaaugg auguuuugcu cccug        55

<210> SEQ ID NO 51
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 15
      and 22 are 2'OMe; a's at positions 16-17, 19-20 and 24 are 2'OMe;
      linkage at positions 55 and 56 is 3'-3'.

<400> SEQUENCE: 51
gggaggacga ugcggaacaa ugcacucguc gccguaaugg auguuuugcu cccug      55

<210> SEQ ID NO 52
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 38,
      41 and 44 are 2'OMe; linkage at positions 55 and 56 is 3'-3'.

<400> SEQUENCE: 52
gggaggacga ugcggaacaa ugcacucguc gccguaaugg auguuuugcu cccug      55

<210> SEQ ID NO 53
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions
      39-40, 43 and 48 are 2'OMe; a's at positions 36-37 and 41 are
      2'OMe; linkage at positions 55 and 56 is 3'-3'.

<400> SEQUENCE: 53
gggaggacga ugcggaacaa ugcacucguc gccguaaugg auguuuugcu cccug      55

<210> SEQ ID NO 54
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5-6, 9, 12, 14-15, 22, 28, 31, 34, 39-40, 43, 48 and 55 are 2'OMe.
<221> NAME/KEY: modified_base
<222> LOCATION: (1)..(55)
<223> OTHER INFORMATION: A's at positions 7, 10, 16-17, 19-20, 24,
      36-37, and 41 are 2'OMe; linkage at positions 55 and 56 is 3'-3'.

<400> SEQUENCE: 54
gggaggacga ugcggaacaa ugcacucguc gccguaaugg auguuuugcu cccug      55

<210> SEQ ID NO 55
<211> LENGTH: 55
<212> TYPE: RNA
<213> ORGANISM: Artificial Sequence
<220> FEATURE:

<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5-6, 9, 12, 14-15, 22, 39-40, 43, 48 and 55 are 2'OMe; a's at
      positions 4,7, 10, 16-17,19-20, 24-36-37, 40 are 2'OMe.
<221> NAME/KEY: modified_base
<222> LOCATION: (1)..(55)
<223> OTHER INFORMATION: Linkage at positions 55 and 56 is 3'-3'.

<400> SEQUENCE: 55
gggaggacga ugcggaacaa ugcacucguc gccguaaugg auguuugcu cccug      55

<210> SEQ ID NO 56
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5-6, 15, 22, 39-40, 43, 48 and 55 are 2'OMe; a's at positions 4,
      16-17,19-20, 24 36-37 and 40 are 2'OMe; linkage at positions 55
      and 56 is 3'-3'.

<400> SEQUENCE: 56
gggaggacga ugcggaacaa ugcacucguc gccguaaugg auguuugcu cccug      55

<210> SEQ ID NO 57
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5, 15, 22, 39-40, 43, 48, and 55 are 2'OMe; a's at positions 4, 7,
      16-17, 19-20, 24, 36-37 and 40 are 2'OMe; linkage at positions 55
      and 56 is 3'-3'.

<400> SEQUENCE: 57
gggaggacga ugcggaacaa ugcacucguc gccguaaugg auguuugcu cccug      55

<210> SEQ ID NO 58
<211> LENGTH: 55
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(55)
<223> OTHER INFORMATION: All pyrimidines are 2'F; g's at positions 1-3,
      5, 9, 15, 22, 39-40, 43, 48 and 55 are 2'OMe; a's at positions 4,
      16-17, 19-20, 24, 36-37 and 41 are 2'OMe; linkage at positions 55
      and 56 is 3'-3'.

<400> SEQUENCE: 58
gggaggacga ugcggaacaa ugcacucguc gccguaaugg auguuugcu cccug      55

<210> SEQ ID NO 59
<211> LENGTH: 55
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(55)
<223> OTHER INFORMATION: All pyrimidines are 2'F; g's at positions 1-3,
       5, 15, 22, 39-40, 43, 48 and 55 are 2'OMe; a's at positions 4, 10,
       16-17, 19-20, 24, 36-37, and 41 are 2'OMe; linkage at positions 55
       and 56 is 3'-3'.

<400> SEQUENCE: 59
gggaggacga ugcggaacaa ugcacucguc gccguaaugg auguuuugcu cccug         55

<210> SEQ ID NO 60
<211> LENGTH: 55
<212> TYPE: RNA
<213> ORGANISM: Artificial Sequence
<220> FEATURE:
<223> OTHER INFORMATION: Description of Artificial Sequence: Synthetic
       Sequence
<221> NAME/KEY: modified_base
<222> LOCATION: (1)..(55)
<223> OTHER INFORMATION: All pyrimidines are 2'F; g's at positions 1-3,
       5, 12, 14-15, 22, 39-40, 43, 48 and 55 are 2'OMe; a's at positions
       4, 16-17, 19-20, 24, 36-37 and 41 are 2'OMe; linkage at positions
       55 and 56 is 3'-3'.

<400> SEQUENCE: 60
gggaggacga ugcggaacaa ugcacucguc gccguaaugg auguuuugcu cccug         55

<210> SEQ ID NO 61
<211> LENGTH: 55
<212> TYPE: RNA
<213> ORGANISM: Artificial Sequence
<220> FEATURE:
<223> OTHER INFORMATION: Description of Artificial Sequence: Synthetic
       Sequence
<221> NAME/KEY: modified_base
<222> LOCATION: (1)..(55)
<223> OTHER INFORMATION: All pyrimidines are 2'F; g's at positions 1-3,
       6, 15, 22, 28, 39-40, 43, 48, and 55 are 2'OMe; a's at positions
       4, 16-17, 19-20, 24, 36-37 and 40 are 2'OMe; linkage at positions
       55 and 56 is 3'-3'.

<400> SEQUENCE: 61
gggaggacga ugcggaacaa ugcacucguc gccguaaugg auguuuugcu cccug         55

<210> SEQ ID NO 62
<211> LENGTH: 55
<212> TYPE: RNA
<213> ORGANISM: Artificial Sequence
<220> FEATURE:
<223> OTHER INFORMATION: Description of Artificial Sequence: Synthetic
       Sequence
<221> NAME/KEY: modified_base
<222> LOCATION: (1)..(55)
<223> OTHER INFORMATION: All pyrimidines are 2'F; g's at positions 1-3,
       5, 15, 22, 39-40, 43, 48 and 55 are 2'OMe; a's at positions 4,
       16-17, 19-20, 27, 36-37 and 40 are 2'OMe; linkage at positions 55
       and 56 is 3'-3'.

<400> SEQUENCE: 62
gggaggacga ugcggaacaa ugcacucguc gccguaaugg auguuuugcu cccug         55

<210> SEQ ID NO 63
<211> LENGTH: 55
<212> TYPE: RNA
<213> ORGANISM: Artificial Sequence
<220> FEATURE:
<223> OTHER INFORMATION: Description of Artificial Sequence: Synthetic
       Sequence
<221> NAME/KEY: modified_base
<222> LOCATION: (1)..(55)

```
<223> OTHER INFORMATION: All pyrimidines are 2'F; g's at positions 1-3,
      5, 15, 22, 39-40, 43, 48 and 55 are 2'OMe; a's at positions 4,
      16-17, 19-20, 24, 36-37, and 40 are 2'OMe; linkage at positions 55
      and 56 is 3'-3'.

<400> SEQUENCE: 63
gggaggacga ugcggaacaa ugcacucguc gccguaaugg auguuuugcu cccug       55

<210> SEQ ID NO 64
<211> LENGTH: 39
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(39)
<223> OTHER INFORMATION: All pyrimidines are 2'F; g's at positions 2-3,
      5-6, 23-24, 27, 32, and 39 are 2'OMe; a's at positions 4, 7,
      20-21, and 25 are 2'OMe; N at position 10 is (CH2CH2O).
<221> NAME/KEY: modified_base
<222> LOCATION: (1)..(39)
<223> OTHER INFORMATION: Linkage at positions 38 and 40 is 3'-3'; n at
      position 10 is A, C, G or U.

<400> SEQUENCE: 64
gggaggacgn cgucgccgua auggauguuu ugcucccug                        39

<210> SEQ ID NO 65
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; g's at positions 2-3,
      5-6, 23-24, 27 and 32 are 2'OMe; a's at positions 4, 7, 20-21, and
      25 are 2'OMe; N at position 10 is (CH2CH2O); linkage at positions
      34 and 35 is 3'-3'.
<221> NAME/KEY: modified_base
<222> LOCATION: (1)..(34)
<223> OTHER INFORMATION: N at position 10 is A, C, G or U.

<400> SEQUENCE: 65
gggaggacgn cgucgccgua auggauguuu ugcu                             34
```

TENASCIN-C NUCLEIC ACID LIGANDS

RELATED APPLICATIONS

This application is a Divisional of U.S. patent application Ser. No. 09/364,902, filed Jul. 29, 1999, now U.S. Pat. No. 6,232,071, which is a Continuation-in-Part of U.S. patent application Ser. No. 08/434,425, filed May 3, 1995, entitled Systematic Evolution of Ligands by Exponential By Enrichment: Tissue SELEX," now U.S. Pat. No. 5,789,157, which is a Continuation-in Part of U.S. patent application Ser. No. 07/714,131, filed Jun. 10, 1991, entitled "Nucleic Acid Ligands," now U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment," now abandoned, and U.S. patent application Ser. No. 07/964,624, filed Oct. 21, 1992, entitled "Nucleic Acid Ligands to HIV-RT and HIV-1 Rev", now U.S. Pat. No. 5,496,938. This application is also a Continuation-in-Part of U.S. patent application Ser. No. 08/993,765, filed Dec. 18, 1997, entitled "Nucleotide Based Prodrugs."

FIELD OF THE INVENTION

Described herein are high affinity nucleic acid ligands to tenascin-C. Also described herein are methods for identifying and preparing high affinity nucleic acid ligands to tenascin-C. The method used herein for identifying such nucleic acid ligands is called SELEX, an acronym for Systematic Evolution of Ligands by Exponential enrichment. Further disclosed are high affinity nucleic acid ligands to tenascin-C. Further disclosed are RNA ligands to tenascin-C. Also included are oligonucleotides containing nucleotide derivatives chemically modified at the 2'-positions of the purines and pyrimidines. Additionally disclosed are RNA ligands to tenascin-C containing 2'-F and 2'OMe modifications. The oligonucleotides of the present invention are useful as diagnostic and/or therapeutic agents.

BACKGROUND OF THE INVENTION

Tenascin-C is a 1.1–1.5 million Da, hexameric glycoprotein that is located primarily in the extracellular matrix. Tenascin-C is expressed during embryogenesis, wound healing, and neoplasia, suggesting a role for this protein in tissue remodeling (Erickson & Bourdon, (1989) *Ann Rev Cell Biol* 5:71–92). Neoplastic processes also involve tissue remodeling, and tenascin-C is over-expressed in many tumor types including carcinomas of the lung, breast, prostate, and colon, astrocytomas, glioblastomas, melanomas, and sarcomas (Soini et at., (1993) *Am J Clin Pathol* 100(2):145–50; Koukoulis et al., (1991) *Hum Pathol* 22(7):636–43; Borsi et al., (1992) *Int J Cancer* 52(5): 688–92; Koukoulis et al., (1993) *J Submicrosc Cytol Pathol* 25(2):285–95; Ibrahim et al., (1993) *Hum Pathol* 24(9): 982–9; Riedi et al., (1998) *Dis Colon Rectum* 41(1):86–92; Tuominen & Kallioinen (1994) *J Cutan Pathol* 21(5):424–9; Natal; et al., (1990) *Int J Cancer* 46(4):586–90; Zagzag et al., (1995) *Cancer Res* 55(4):907–14; Hasegawa et al., (1997) *Acta Neuropathol (Berl)* 93(5):431–7; Saxon et al., (1997) *Pediatr Pathol Lab Med* 17(2):259–66; Hasegawa et al., (1995) *Hum Pathol* 26(8):838–45). In addition, tenascin-C is overexpressed in hyperproliferative skin diseases, e.g. psoriasis (Schalkwijk et al., (1991) *Br J Dermatol* 124(1):13–20), and in atherosclerotic lesions (Fukumoto et al., (1998) *J Atheroscler Thromb* 5(1):29–35; Wallner et al., (1999) *Circulation* 99(10):1284–9). Radiolabeled antibodies that bind tenascin-C are used for imaging and therapy of tumors in clinical settings (Paganelli et al., (1999) *Eur Nucl Med* 26(4):348–57; Paganelli et al., (1994) *Eur J Nucl Med* 21(4):314–21; Bigner et al., (1998) *J Clin Oncol* 16(6):2202–12; Merlo et al., (1997) *Int J Cancer* 71(5):810–6).

Aptamers against tenascin-C have potential utility for cancer diagnosis and therapy, as well as for diagnosis and therapy of atheroslerosis and therapy of psoriasis. Relative to antibodies, aptamers are small (7–20 kDa), clear very rapidly from blood, and are chemically synthesized. Rapid blood clearance is important for in vivo diagnostic imaging, where blood levels are a primary determinant of background that obscures an image. Rapid blood clearance may also be important in therapy, where blood levels may contribute to toxicity. SELEX technology allows rapid aptamer isolation, and chemical synthesis enables facile and site-specific conjugation of aptamers to a variety of inert and bioactive molecules. An aptamer to tenascin-C would therefore be useful for tumor therapy or in vivo or ex vivo diagnostic imaging and/or for delivering a variety of therapeutic agents complexed with the tenascin-C nucleic acid ligand for treatment of disease conditions in which tenascin-C is expressed.

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO 91/19813) entitled "Methods for Identifying Nucleic Acid Ligands," each of which is specifically incorporated by reference herein in its entirety. Each of these applications, collectively referred to herein as the SELEX patent applications, describes a fundamentally novel method for making a nucleic acid ligand to any desired target molecule. The SELEX process provides a class of products which are referred to as nucleic acid ligands or aptamers, each having a unique sequence, and which have the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets in the SELEX method. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX" describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow lo the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patents and applications which describe modifications of the basic SELEX procedure are specifically incorporated by reference herein in their entirety.

SUMMARY OF THE INVENTION

The present invention describes a method for isolating nucleic acid ligands that bind to tenascin-C with high specificity. Further described herein are nucleic acid ligands to tenascin-C. Also described herein are high affinity RNA ligands to tenascin-C. Further described are 2'fluoro-modified pyrimidine and 2'OMe-modified purine RNA ligands to tenascin-C. The method utilized herein for identifying such nucleic acid ligands is called SELEX, an acronym for Systematic Evolution of Ligands by Exponential enrichment. Included herein are the ligands that are shown in Tables 3 and 4 and FIG. 2.

Further included in this invention is a method for detecting the presence of a disease that is expressing tenascin-C in a biological tissue that may contain the disease. Still further included in this invention is a method for detecting the presence of a tumor that is expressing tenascin-C in a biological tissue that may contain the tumor. Further included in this invention is a complex for use in in vivo or ex vivo diagnostics. Still further included in this invention is a method for delivering therapeutic agents for the treatment or prophylaxis of diseased tissues that express tenascin-C. Still further included in this invention is a complex for use in delivering therapeutic agents for treatment or prophylaxis of diseased tissues that express tenascin-C.

DETAILED DESCRIPTION OF THE PREFERRED EMBODIMENTS

The central method utilized herein for identifying nucleic acid ligands to tenascin-C is called the SELEX process, an acronym for Systematic Evolution of Ligands by Exponential enrichment and involves (a) contacting the candidate mixture of nucleic acids with tenascin-C (b) partitioning between members of said candidate mixture on the basis of affinity to tenascin-C, and c) amplifying the selected molecules to yield a mixture of nucleic acids enriched for nucleic acid sequences with a relatively higher affinity for binding to tenascin-C. The invention includes RNA ligands to tenascin-C. This invention further includes the specific RNA ligands to tenascin-C shown in Tables 3 and 4 and FIG. 2. More specifically, this invention includes nucleic acid sequences that are substantially homologous to and that have substantially the same ability to bind tenascin-C as the specific nucleic acid ligands shown in Tables 3 and 4 and FIG. 2. By substantially homologous it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. Substantially the same ability to bind tenascin-C means that the affinity is within one or two orders of magnitude of the affinity of the ligands described herein. It is well within the skill of those of ordinary skill in the art to determine whether a given sequence—substantially homologous to those specifically described herein—has the same ability to bind tenascin-C.

Figure 2:
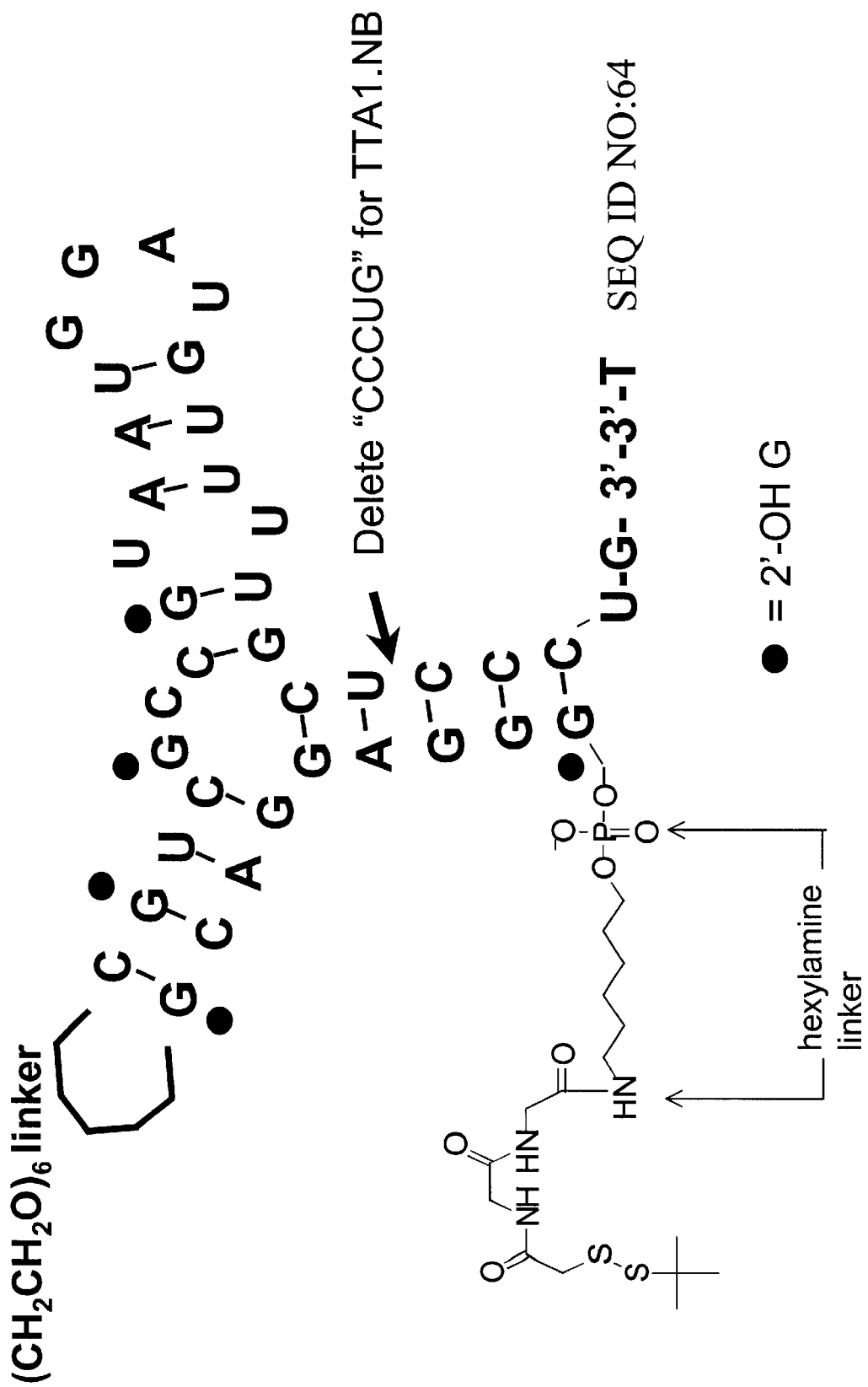
FIG. 2 shows proposed secondary structure of aptamers TTA1 and TTA1.NB. Included in the figure is the conjugation of the aptamers with Tc-99m. All A's are 2'OMe modified. All G's, except as indicated, are 2'OMe modified. All C's and U's are 2'F modified.

A review of the sequence homologies of the nucleic acid ligands of tenascin-C shown in Tables 3 and 4 and FIG. 2 shows that sequences with little or no primary homology may have substantially the same ability to bind tenascin-C. For these reasons, this invention also includes Nucleic Acid Ligands that have substantially the same postulated structure or structural motifs and ability to bind tenascin-C as the nucleic acid ligands shown in Tables 3 and 4 and FIG. 2. Substantially the same structure or structural motifs can be postulated by sequence alignment using the Zukerfold program (see Zuker (1989) Science 244:48–52). As would be known in the art, other computer programs can be used for predicting secondary structure and structural motifs. Substantially the same structure or structural motif of Nucleic Acid Ligands in solution or as a bound structure can also be postulated using NMR or other techniques as would be known in the art.

Further included in this invention is a method for detecting the presence of a disease that is expressing tenascin-C in a biological tissue which may contain the disease by the method of (a) identifying a nucleic acid ligand from a candidate mixture of nucleic acids, the nucleic acid ligand being a ligand of tenascin-C, by the method comprising (i) contacting a candidate mixture of nucleic acids with tenascin-C, wherein nucleic acids having an increased affinity to tenascin-C relative to the candidate mixture may be partitioned from the remainder of the candidate mixture; (ii) partitioning the increased affinity nucleic acids from the remainder of the candidate mixture; (iii) amplifying the increased affinity nucleic acids to yield a mixture of nucleic acids with relatively higher affinity and specificity for binding to tenascin-C, whereby a nucleic acid ligand of tenascin-C is identified; (b) attaching a marker that can be used in in vivo or ex vivo diagnostics to the nucleic acid ligand identified in step (iii) to form a marker-nucleic acid ligand complex; (c) exposing a tissue which may contain the disease to the marker-nucleic acid ligand complex; and (d) detecting the presence of the marker-nucleic acid ligand in the tissue, whereby a disease expressing tenascin-C is identified.

It is a further object of the present invention to provide a complex for use in in vivo or ex vivo diagnostics comprising one or more tenascin-C nucleic acid ligands and one or more markers. Still further included in this invention is a method for delivering therapeutic agents for the treatment or prophylaxis of disease conditions in which tenascin-C is expressed. Still further included in this invention is a complex for use in delivering therapeutic agents for treatment or prophylaxis of disease conditions in which tenascin-C is expressed.

Definitions

Various terms are used herein to refer to aspects of the present invention. To aid in the clarification of the description of the components of this invention, the following definitions are it provided:

As used herein, "nucleic acid ligand" is a non-naturally occurring nucleic acid having a desirable action on a target. Nucleic acid ligands are often referred to as "aptamers." The target of the present invention is tenascin-C, hence the term tenascin-C nucleic acid ligand. A desirable action includes but is not limited to binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands are identified from a candidate mixture of nucleic acids, said nucleic acid ligand being a ligand of a tenascin-C, by the method comprising: a) contacting the candidate mixture with tenascin-C, wherein nucleic acids having an increased affinity to tenascin-C relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids (see U.S. patent application Ser. No. 08/434,425, filed May 3, 1995, now U.S. Pat. No. 5,789,157, which is hereby incorporated herein by reference).

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to tenascin-C.

The SELEX methodology is described in the SELEX patent applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX target is tenascin-C.

"Complex" as used herein means the molecular entity formed by the covalent linking of one or more tenascin-C nucleic acid ligands with one or more markers. In certain embodiments of the present invention, the complex is depicted as A-B-Y, wherein A is a marker; B is optional, and comprises a linker; and Y is a tenascin-C nucleic acid ligand.

"Marker" as used herein is a molecular entity or entities that when complexed with the tenascin-C nucleic acid ligand, either directly or through a linker(s) or spacer(s), allows the detection of the complex in an in vivo or ex vivo setting through visual or chemical means. Examples of markers include, but are not limited to radionuclides, including Tc-99m, Re-188, Cu-64, Cu-67, F-18, $^{125}$I, $^{131}$I, $^{32}$P, $^{186}$Re; all fluorophores, including fluorescein, rhodamine, Texas Red; derivatives of the above fluorophores, including Rhodamine-Red-X; magnetic compounds; and biotin.

As used herein, "linker" is a molecular entity that connects two or more molecular entities through covalent bond or non-covalent interactions, and can allow spatial separation of the molecular entities in a manner that preserves the functional properties of one or more of the molecular entities. A linker can also be known as a spacer. Examples of a linker include, but are not limited to, the $(CH_2CH_2O)_6$ and hexylamine structures shown in FIG. 2.

"Therapeutic" as used herein, includes treatment and/or prophylaxis. When used, therapeutic refers to humans and other animals.

"Covalent Bond" is the chemical bond formed by the sharing of electrons.

"Non-covalent interactions" are means by which molecular entities are held together by interactions other than Covalent Bonds including ionic interactions and hydrogen bonds.

In the preferred embodiment, the nucleic acid ligands of the present invention are derived from the SELEX methodology. The SELEX process is described in U.S. patent application Ser. No. 07/536,428, entitled Systematic Evolution of Ligands by Exponential Enrichment, now abandoned, U.S. Pat. No. 5,475,096 entitled Nucleic Acid Ligands and U.S. Pat. No. 5,270,163 (see also WO 91/19813) entitled Methods for Identifying Nucleic Acid Ligands. These applications, each specifically incorporated herein by reference, are collectively called the SELEX patent applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding, a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796 both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX" all describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938 methods are described for obtaining improved Nucleic Acid Ligands after the SELEX process has been performed. This patent, entitled "Nucleic Acid Ligands to HIV-RT and HIV1 Rev," is specifically incorporated herein by reference.

U.S. patent application Ser. No. 08/434,425, entitled "Systematic Evolution of Ligands by Exponential Enrichment: Tissue SELEX," filed May 3, 1995, now U.S. Pat. No. 5,789,157, describes methods for identifying a nucleic acid ligands to a macromolecular component of a tissue, including cancer cells, and the nucleic acid ligands so identified. This patent is specifically incorporated herein by reference.

One potential problem encountered in the diagnostic or therapeutic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned, and U.S. Pat. No. 5,660,985, both entitled "High Affinity Nucleic Acid Ligands Containing Modified Nucleotides", which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety.

The tenascin-C aptamers of the invention bind to the heparin binding site of the tenascin-C COOH terminus.

In certain embodiments of the present invention, the Nucleic Acid ligands to tenascin-C described herein are useful for diagnostic purposes and can be used to image pathological conditions (such as human tumor imaging). In addition to diagnosis, the tenascin-C nucleic acid ligands are useful in the prognosis and monitoring of disease conditions in which tenascin-C is expressed.

Diagnostic agents need only be able to allow the user to identify the presence of a given target at a particular locale or concentration. Simply the ability to form binding pairs with the target may be sufficient to trigger a positive signal for diagnostic purposes. Those skilled in the art would be able to adapt any tenascin-C nucleic acid ligand by procedures known in the art to incorporate a marker in order to track the presence of the nucleic acid ligand. Such a marker could be used in a number of diagnostic procedures, such as detection of primary and metastatic tumors and atherosclerotic lesions. The labeling marker exemplified herein is technetium-99m; however, other markers such as additional radionuclides, magnetic compounds, fluorophores, biotin, and the like can be conjugated to the tenascin-C nucleic acid ligand for imaging in an in vivo or ex vivo setting disease conditions in which tenascin-C is expressed (e.g., cancer, atherosclerosis, and psoriasis). The marker may be covalently bound to a variety of positions on the tenascin-C nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the tenascin-C nucleic acid ligand. In embodiments where the marker is technetium-99m, preferably it is bonded to the 5' or 3' hydroxyl of the phosphate group thereof or to the 5 position of a modified pyrimidine. In the most preferred embodiment, the marker is bonded to the 5' hydroxyl of the phosphate group of the nucleic acid ligand with or without a linker. In another embodiment, the marker is conjugated to the nucleic acid ligand by incorporating a pyrimidine containing a primary amine at the 5 position, and use of the amine for conjugation to the marker. Attachment of the marker can be done directly or with the utilization of a linker. In the embodiment where technetium-99m is used as the marker, the preferred linker is a hexylamine linker as shown in FIG. 2.

In other embodiments, the tenascin-C nucleic acid ligands are useful for the delivery of therapeutic compounds (including, but not limited to, cytotoxic compounds, immune enhancing substances and therapeutic radionuclides) to tissues or organs expressing tenascin-C. Disease conditions in which tenascin-C may be expressed include, but are not limited to, cancer, atherosclerosis, and psoriasis. Those skilled in the art would be able to adapt any tenascin-C nucleic acid ligand by procedures known in the art to incorporate a therapeutic compound in a complex. The therapeutic compound may be covalently bound to a variety of positions on the tenascin-C nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the tenascin-C nucleic acid ligand. In the preferred embodiment, the therapeutic agent is bonded to the 5' amine of the nucleic acid ligand. Attachment of the therapeutic agent can be done directly or with the utilization of a linker. In embodiments in which cancer is the targeted disease, 5-fluorodeoxyuracil or other nucleotide analogs known to be active against tumors can be incorporated internally into existing U's within the tenascin-C nucleic acid ligand or can be added internally or conjugated to either terminus either directly or through a linker. In addition, both pyrimidine analogues 2'2'-diFluorocytidine and purine analogues (deoxycoformycin) can be incorporated. In addition, U.S. application Ser. No. 08/993,765, filed Dec. 18, 1997, incorporated herein by reference in its entirety, describes, inter alia, nucleotide-based prodrugs comprising nucleic acid ligands directed to a tumor, for example tenascin-C, for precisely localizing chemoradiosensitizers, and radiosensitizers and radionuclides and other radiotherapeutic agents to the tumor.

It is also contemplated that both the marker and therapeutic agent may be associated with the tenascin-C nucleic acid ligand such that detection of the disease condition and delivery of the therapeutic agent is accomplished together in one aptamer or as a mixture of two or more different modified versions of the same aptamer. It is also contemplated that either or both the marker and/or the therapeutic agent may be associated with a non-immunogenic, high molecular weight compound or lipophilic compound, such as a liposome. Methods for conjugating nucleic acid ligands with lipophilic compounds or non-immunogenic compounds in a diagnostic or therapeutic complex are described in U.S. patent application Ser. No. 08/434,465, filed May 4, 1995, entitled "Ligand Nucleic Acid Complexes," which is incorporated herein in its entirety.

The therapeutic or diagnostic compositions described herein may be administered parenterally by injection (e.g., intravenous, subcutaneous, intradermal, intralesional), although other effective administration forms, such as intraarticular injection, inhalant mists, orally active formulations, transdermal iontophoresis or suppositories, are also envisioned. They may also be applied locally by direct injection, can be released from devices, such as implanted stents or catheters, or delivered directly to the site by an infusion pump. One preferred carrier is physiological saline solution, but it is contemplated that other pharmaceutically acceptable carriers may also be used. In one embodiment, it is envisioned that the carrier and the tenascin-C nucleic acid ligand complexed with a therapeutic compound constitute a physiologically-compatible, slow release formulation. The primary solvent in such a carrier may be either aqueous or non-aqueous in nature. In addition, the carrier may contain other pharmacologically acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the tenascin-C nucleic acid ligand. Such excipients are those substances usually and customarily employed to formulate dosages for parental administration in either unit dose or multi-dose form.

Once the therapeutic or diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to administration. The manner of administering formulations containing tenascin-C nucleic acid ligands for systemic delivery may be via subcutaneous, intramuscular, intravenous, intraarterial, intranasal or vaginal or rectal suppository.

The following examples are provided to explain and illustrate the present invention and are not to be taken as limiting of the invention. Example 1 describes the materials and experimental procedures used in Example 2 for the generation of RNA ligands to tenascin-C. Example 2 describes the RNA ligands to tenascin-C and the predicted secondary structure of a selected nucleic acid ligand. Example 3 describes the determination of minimal size necessary for high affinity binding of a selected nucleic acid ligand, and substitution of 2'-OH purines with 2'-OMe purines. Example 4 describes the biodistribution of Tc-99m labeled tenascin-C nucleic acid ligands in tumor-bearing mice. Example 5 describes the use of a fluorescently labeled tenascin-C nucleic acid ligand to localize tenascin-c within tumor tissue.

EXAMPLES

Example 1

Use of SELEX to obtain nucleic acid ligands to tenascin-C and to U251 glioblastoma cells Materials and Methods Tenascin-C was purchased from Chemicon (Temecula, Calif.). Single-stranded DNA-primers and templates were synthesized by Operon Technologies Inc. (Alameda, Calif.).

The SELEX-process has been described in detail in the SELEX patent applications. In brief, double-stranded transcription templates were prepared by Klenow fragment extension of 40N7a ssDNA:
5'- TCGCGCGAG-CGTCTG[40N] CCGCATCGTCCTCCC 3' (SEQ ID NO:1)
using the 5N7 primer:
5-TAATACGACTCACTATAGGGAGGACGATGCGG-3' (SEQ ID NO:2)
which contains the T7 polymerase promoter (underlined). RNA was prepared with T7 RNA polymerase as described previously in Fitzwater, T., and Polisky, B. 1996. A SELEX primer. *Methods Enzymol.* 267, 275–301, incorporated herein by reference in its entirety. All transcription reactions were performed in the presence of pyrimidine nucleotides that were 2'-fluoro (2'-F) modified on the sugar moiety. This substitution confers enhanced resistance to ribonucleases that utilize the 2'-hydroxyl moiety for cleavage of the phosphodiester bond. Specifically, each transcription mixture contained 3.3 mM 2'-F UTP and 3.3 mM 2'-F CTP along with 1 mM GTP and ATP. The initial randomized RNA library thus produced comprised $3 \times 10^{14}$ molecules. The affinities of individual ligands for tenascin-C were determined by standard methods using nitrocellulose filter partitioning (Tuerk C, Gold L. Science 1990 August 3;249(4968):505–10).

For each round of SELEX, Lumino plates (Labsystems, Needham Heights, Mass.) were coated for 2 hours at room temperature with 200 µl Dulbecco's PBS containing tenascin-C concentrations as shown in Table 1. After coating, wells were blocked using HBSMC+ buffer [20 mM Hepes, pH 7.4, 137 mM NaCl, 1 mM $CaCl_2$, 1 mM $MgCl_2$ and 1 g/liter human serum albumin (Sigma, fraction V) for rounds 1 to 6 while for rounds 7 and 8 wells were blocked HBSMC+ buffer containing 1 g/liter casein (I-block; Tropix). Binding and wash buffer consisted of HBSMC+ buffer containing 0.05% Tween 20. For each SELEX round, RNA was diluted into 100 µl of binding buffer and allowed to incubate for 2 hours at 37° C. in the protein coated wells that were pre-washed with binding buffer. After binding, six washes of 200 µl each were performed. Following the wash step, the dry well was placed on top of a 95° C. heat block for 5 minutes. Standard AMV reverse transcriptase reactions (50 µl) were performed at 48° C. directly in the well and the reaction products utilized for standard PCR and transcription reactions. Two synthetic primers 5N7 (see above) and 3N7a: 5'-TCGCGCGAGTCGTCTG-3' (SEQ ID NO:3)

For cell SELEX, U251 human glioblastoma cells (Hum. Hered., 1971, 21: 238) were grown to confluence in Dulbecco's Modified Eagle's Medium supplemented with 10% fetal calf serum (GIBCO BRL, Gaithersburg, Md.) on six-well tissue culture plates (Becton Dickinson Labware, Lincoln Park, N.J.) and washed three times using Dulbecco's PBS supplemented with CaCl, (DPBS, GIBCO BRL) buffer. RNA labeled internally by transcription (Fitzwater, 1996, supra) was incubated with the cells at 37 degrees for one hour. The labeled RNA was then removed, and the cells were washed six times for ten minutes each at 37 degrees with DPBS. DPBS containing 5 mM EDTA was then added and incubated with the cells for 30 minutes to elute bound RNAs that remained after the washing steps. This RNA was quantitated by a standard liquid scintillation counting protocol and amplified using RT-PCR.

Binding assays for the U251 cells. Internally labeled RNA was incubated at increasing concentrations with confluent U251 cells in six-well tissue culture plates (Becton Dickinson Labware, Lincoln Park, N.J.) at 37 degrees for 60 min. Unbound RNA was washed away using three 10 minute washes with $DPBS+CaCl_2$ at 37 degrees, and bound RNA was collected by disrupting the cells using Trizol (Gibco BRL, Gaithersburg, Md.). Bound RNA was quantitated by liquid scintillation counting.

Cloning and Sequencing. Amplified affinity enriched oligonucleotide pools were purified on an 8% polyacrylamide gel, reverse transcribed into ssDNA and the DNA amplified by the polymerase chain reaction (PCR) using primers containing BamH1 and HindIII restriction endonuclease sites. PCR fragments were cloned, plasmids prepared and sequence analyses performed according to standard techniques (Sambrook et al. (1989) *Molecular Cloning: A Laboratory Manual*, $2^{nd}$ Ed. 3 vols., Cold Spring Harbor Laboratory Press, Cold Spring Harbor).

Example 2

RNA ligands to tenascin-C

Nucleic Acid Ligands to U25 I cells were obtained by the SELEX process and are described in U.S. patent application Ser. No. 08/434,425, entitled "Systematic Evolution of Ligands by Exponential Enrichment: Tissue SELEX," filed May 3, 1995, now U.S. Pat. No. 5,789,157. Subsequently it was determined that the ligands that were obtained were tenascin-C nucleic acid ligands.

To obtain oligonucleotide ligands against human tenascin-C, eight rounds of SELEX were performed using the randomized nucleotide library as described above in Materials and Methods. RNA and protein input into each round is shown in Table 1. After 8 rounds of to SELEX, the affinity of the oligonucleotide pool for tenascin-C was 10 nM, and this affinity did not increase with additional SELEX rounds.

Figure 1:
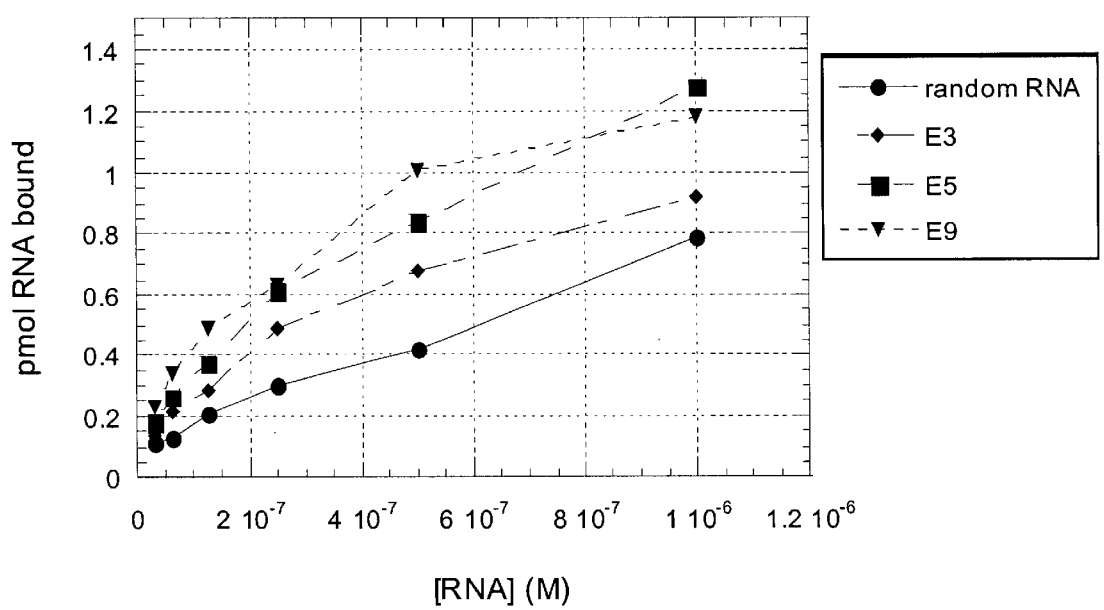
FIG. 1 shows binding of Cell SELEX RNA pools to U251 cells.

To obtain ligands to U251 glioblastoma cells, nine rounds of SELEX were performed using the randomized nucleotide library. After nine rounds of binding to U251 cells and EDTA elution, rounds 3, 5 and 9 were tested for their ability to bind to U251 cells. FIG. 1 shows that as the number of SELEX rounds increases, the amount of bound RNA also increases at a particular-concentration. Because of the complexity of the target tissue, it was not possible to estimate the affinity of the oligonucleotide pools for the unknown target molecules(s) on these cells.

The E9 pool (nine rounds of binding and EDTA elution from U251 cells) was then used as a starting point for a SELEX against purified tenascin-C. Two rounds of SELEX using purified tenascin-C were performed as described above. Input protein and RNA concentrations for two rounds of SELEX (E9P1 and E9P2) are described in Table 2.

In summary, three different SELEX experiments were performed: an experiment using purified tenascin-C as the target, an experiment using U251 glioblastoma cells as the target, and an experiment in which the SELEX pool from the U251 glioblastoma cells was used to initiate a SELEX experiment using purified tenascin-C as the target.

All three SELEX experiments were analyzed by cloning and sequencing ligands from round 8 of the purified tenascin-C SELEX ("TN" sequences), from round 9 of the U251 cell SELEX ("E9" sequences), and from round 2 of the U251/tenascin-C hybrid SELEX ("E9P2" sequences). The sequences of 34 unique clones are shown in Table 3, and are divided into two major groups: tenascin-C ligands ("TN" and "E9P2" sequences) and U251 cell ligands ("E9" ligands). Among the tenascin-C ligands, the majority of the clones (65 total) represent one of two distinct sequence classes designated Family I and Family II (FIG. 1). Examination of the variable region of the 12 clones in Family I revealed 7 unique sequences that are related through the consensus sequence GACNYUUCCNGCYAC (SEQ ID NO:12). Examination of the variable region of the 18 clones in Family II revealed sequences that share a consensus sequence CGUCGCC (Table 3). The E9 sequences could be grouped into a related set by virtue of conserved GAY and CAU sequences within the variable regions. The remaining sequences did not appear related to other sequences and were classified as orphans. Three sequences predominate, with E9P2-1, E9P2-2, and TN9 represented 14,16, and 10 times respectively. In the "Orphan" category, one sequence, TN18, was represented twice. Overall, these data represent a highly enriched sequence pool.

Most individuals displayed low nanomolar dissociation constants, with the three most prevalent sequences, TN9 and E9P2-1 and -2, having the highest affinities at 5 nM, 2 nM, and 8 nM. (Table 3). These results indicate that the U251 cell SELEX is a repository for aptamers against tenascin-C, and that only two rounds of SELEX were required to isolate the tenascin-specific ligands from the cell SELEX pool. Oligonucleotide ligands against other proteins can be similarly isolated from the E9 pool using purified protein targets.

Example 3

Determination of minimal size of TN9, and substitution of 2'-OH purines with 2'-OMe purines: synthesis of aptamer TTA1

Oligonucleotide synthesis procedures were standard for those skilled in the art (Green LS, Jellinek D, Bell C, Beebe LA, Feistner BD, Gill SC, Jucker FM, Janjic N. Chem Biol 1995 October;2(10):683–95). 2'-fluoro pyrimidine phosphoramidite monomers were obtained from JBL Scientific (San Luis Obispo, Calif.); 2'-OMe purine, 2'-OH purine, hexyl amine, and $(CH_2CH_2O)_6$ monomers, along with the dT polystyrene solid support, were obtained from Glen Research (Sterling, Va.). Aptamer affinities were determined using nitrocellulose filter partitioning (Green et al., supra).

TN9 was chosen for further analysis based on its high affinity for tenascin-C. We first searched for a minimal sequence necessary for high affinity binding. Using standard techniques (Green et al, supra), it was discovered that nucleotides 3' of nucleotide 55 were required for binding to tenascin-C, while no nucleotides could be removed from the 5' end without loss of affinity. To further decrease the TN9's length from 55 nucleotides and retain high affinity binding, we then attempted to define internal deletions of TN9. The first 55 nucleotides of TN9, along with the first 55 nucleotides of related family II ligands TN7, TN21, and TN41, were input into a computer algorithm to determine possible RNA secondary structure foldings (mfold 3.0, accessed at http:H/www.ibc.wustl.edu/zuker/. M. Zuker, D. H. Mathews & D. H. Turner. Algorithms and Thermodynamics for RNA Secondary Structure Prediction: A Practical Guide. In: RNA Biochemistry and Biophysics, J. Barciszewski & B. F. C. Clark, eds., NATO ASI Series, Kluwer Academic Publishers, (1999)). Among many potential RNA foldings predicted by the algorithm, a structure common to each oligonucleotide was found. This structure, represented by oligonucleotide TTA1 in FIG. 2, contains three stems that meet at a single junction, a so-called 3-stem junction. This folding places the most highly conserved nucleotides of family II oligonucleotides at the junction area. In comparing TN9, TN7, TN21, and TN41, the second stem was of variable length and sequence, suggesting that extension of the second stem is not required for binding to tenascin-C. Testing this hypothesis on TN9, we found that nucleotides 10–26 could be replaced with an ethylene glycol linker, $(CH_2CH_2O)_6$. The linker serves as a substitute loop and decreases the size of the aptamer. Additionally, four-nucleotide loops (CACU or GAGA) that replace nucleotides 10–26 produce sequences with high affinity for tenascin-C. It would be well within one skilled in the art to determine other nucleotide loops or other spacers that could replace nucleotides 10–26 to produce sequences with high affinity for tenascin-C.

To increase protection against nuclease activity, purine positions that could be substituted with the corresponding 2'-OMe purines were located. The oligonucleotide was arbitrarily divided into five sectors and all purines within each sector were substituted by the corresponding 2'-OMe purine nucleotide, a total of five oligonucleotides (Table 4, Phase I syntheses). The affinity of each oligonucleotide for tenascin-C was determined, and it was found that all purines within sectors 1,3 and 5 could be substituted without appreciable loss in affinity. Within sectors 2 and 4, individual purines were then substituted with 2'-OMe purines and the effect of affinity was measured (Table 4, Phase III syntheses). From these experiments, it was deduced that substitution of nucleotides G9, G28, G31, and G34, with 2'-OMe G causes loss in affinity for tenascin-C. Therefore these nucleotides remain as 2'-OH purines in the aptamer TTA1.

The aptamer TTA1 (Table 4) was then synthesized with the $(CH_2CH_2O)_6$ (Spacer 18) linker, a 3'—3' dT cap for exonuclease protection, a 5' hexyl amine (Table 4), and all purines as 2'-OMe except the 5 Gs indicated in Table 4. A non-binding control aptamer, TTA1.NB, was generated by deleting 5 nucleotides at the 3' end to produce TTA1.NB. TTA1 binds to tenascin-C with an equilibrium dissociation constant ($K_d$) of 5 nM, while TTA1.NB has a $K_d$ of >5 $\mu$M for tenascin-C.

Nucleotides 10–26 can be replaced by a non-nucleotide ethylene glycol linker. It is therefore likely that TTA1 can be synthesized in two separate pieces, where a break is introduced at the position of the ethylene glycol linker and new 5' and 3' ends are introduced. Subsequent to synthesis, the two molecules will incubated together to allow hybrid formation. This method allows introduction of additional amine groups as well as nucleotides at the new 5' and 3 ends. The new functionalities could be used for bioconjugation. In addition, two-piece synthesis results in increased chemical synthetic yield due to shortening the length of the molecules.

Example 4

Biodistribution of Tc-99m labeled aptamers in tumor-bearing mice

Figure 5:
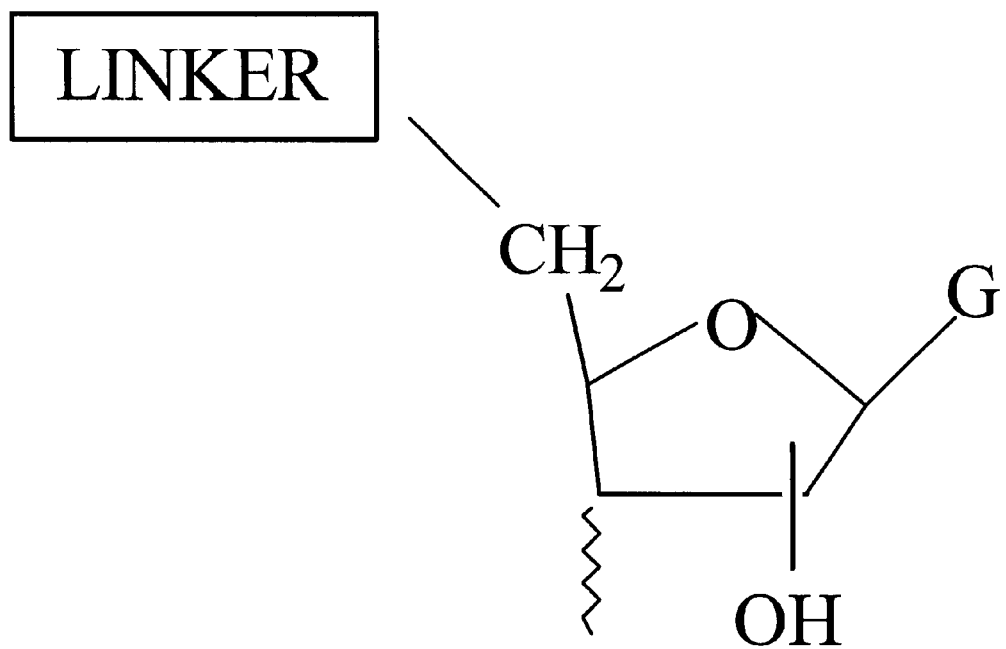
FIG. 5 shows the way in which the Tc-99m and linker is bound through the 5'G of TTA1.

Aptamer biodistribution was tested by conjugating a Tc-99m chelator ($Hi_{15}$; Hilger, C. S., Willis, M. C., Wolters, M. Pieken, W. A. 1998. Tet. Lett 39, 9403–9406) to the 5' end of the oligonucleotide as shown in FIG. 2, and radiolabeling the aptamer with Tc-99m. TTA1 and TTA1.NB were conjugated to $Hi_{15}$ at 50 mg/ml aptamer in 30% dimethylformamide with 5 molar equivalents of $Hi_{15}$-N-hydoxysuccinimide, buffered in 100 mM Na Borate pH 9.3, for 30 minutes at room temperature. Reversed phase HPLC purification yielded $Hi_{15}$-TTA1 and $Hi_{15}$-TTA1.NB. The oligonucleotides were then labeled with Tc-99m in the following manner: to 1 nmole Hi15-aptamer was added 200 $\mu$L of 100 mM NaPO4 buffer, pH 8.5, 23 mg/mL NaTartrate, and 50 µL Tc-99m pertechnetate (5.0 mCi) eluted from a Mo-99 column (Syncor, Denver) within 12 hours of use. The labeling reaction was initiated by the addition of 10 µL 5 mg/mL $SnCl_2$. The reaction mixture was incubated for 15 minutes at 90° C. The reaction was separated from unreacted Tc-99m by spin dialysis through a 30,000 MW cut-off membrane (Centrex, Schleicher & Scheull) with two 300 µL washes. This labeling protocol results in 30–50% of the added 99mTc being incorporated with a specific activity of 2–3 mCi/nmole RNA. The Tc-99m is bound through the 5'G as shown in FIG. 5.

For biodistribution experiments, U251 xenograft tumors were prepared as follows: U251 cells were cultured in Dulbeccos' Modified Eagle's Medium supplemented with 10% v/v fetal calf serum (Gibco BRL, Gaithersburg, Md.). Athymic mice (Harlan Sprague Dawley, Indianapolis, Ind.) were injected subcutaneously with $1 \times 10^6$ U251 cells. When the tumors reached a size of 200–300 mg (1–2 weeks), Tc-99m labeled aptamer was injected intravenously at 3.25 mg/kg. At indicated times, animals were anesthetized using isoflurane (Fort Dodge Animal Health, Fort Dodge, Iowa), blood was collected by cardiac puncture, and the animal was sacrificed and tissues were harvested. Tc-99m levels were counted using a gamma counter (Wallac Qy, Turku, Finland). Aptamer uptake into tissues was measured as the % of injected dose per gram of tissue (% ID/g).

Images of mice were obtained using a gamma camera. Mice were placed onto the camera (Siemens, LEM+) under anesthesia (isoflurane). Data were collected (30 sec to 10 minutes) and analyzed using Nuclear MAC software version 3.22.2 (Scientific Imaging, CA) on a Power MAC G3 (Apple Computer, Calif.).

Biodistribution experiments, Table 5, indicated rapid and specific uptake of the aptamer into tumor tissue; the non-binding aptamer does not remain in the tumor. Blood levels of Tc-99m also cleared rapidly. After three hours, Tc-99m levels brought into the tumor using $Hi_{15}$-TTA1 had a very long half life (>18 hrs). This indicates that once the aptamer penetrates the tumor, the radiolabel carried with it remains in the tumor for long periods of time. Such data indicate that cytotoxic agents, including radionuclides and non-radioactive agents, conjugated to the aptamer will also remain in the tumor with long half lives.

Tc-99m radioactivity also appears in other tissues, notably the small and large intestines. The hepatobiliary clearance pattern seen here can be readily altered by those skilled in the art, for example by altering the hydrophilicity of the Tc-99m chelator, changing the chelator, or changing the radiometal/chelator pair altogether.

Figure 3:
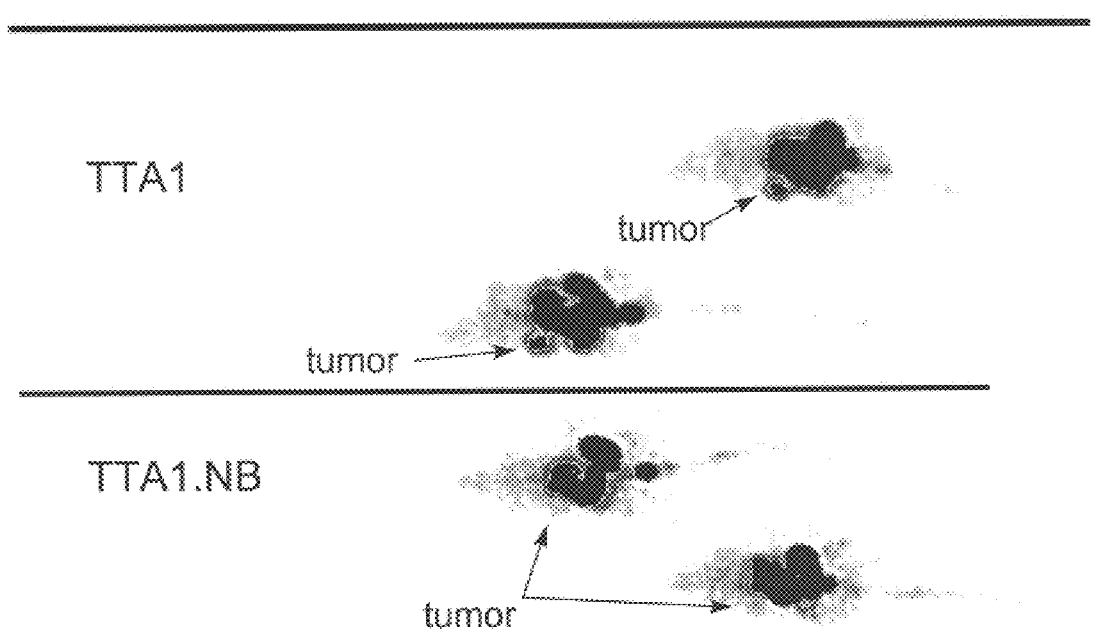
FIG. 3 shows images of U251 tumor xenografts in mice, obtained using Tc-99m-labeled TTA1 and TTA1.NB, three hours post-injection.

Whole animal images were obtained using Tc-99m labeled $Hi_{15}$-TTA1 and at 3 hours post-injection. Images obtained from mice injected with $Hi_{15}$-TTA1, but not from mice injected with $Hi_{15}$-TTA1.NB, clearly show the tumor (FIG. 3). Additional radioactivity is evident in gastrointestinal tract, as predicted by the biodistribution experiments.

Example 5

Use of fluorescently labeled TTA1 to localize tenascin-c within tumor tissue

Materials and Methods.

TTA1 and TTA1.NB were synthesized as described above. Succinimdyl Rhodamine-Red-X (Molecular Probes, Eugene, Oreg.) was conjugated to the 5' amine of the aptamers as described above for $H_{15}$-NHS conjugation. The Rhodamine-Red-X-conjugated aptamers, TTA1-Red and TTA1.NB-Red, were purified by reversed phase HPLC. U251 cell culture and tumor growth in nude mice were as described above. Five nmol of TTA1-Red or TTA1.NB-Red were injected intravenously into nude mice and at the desired time the animal was placed under anesthesia, perfused with 0.9% NaCl, and sacrificed. The tumor was excised and placed in formalin. After 24 hr in formalin, 10 µM sections were cut and Rhodamine-Red-X was detected using a fluorescence microscope (Eclipse E800, Nikon, Japan).

Figure 4:
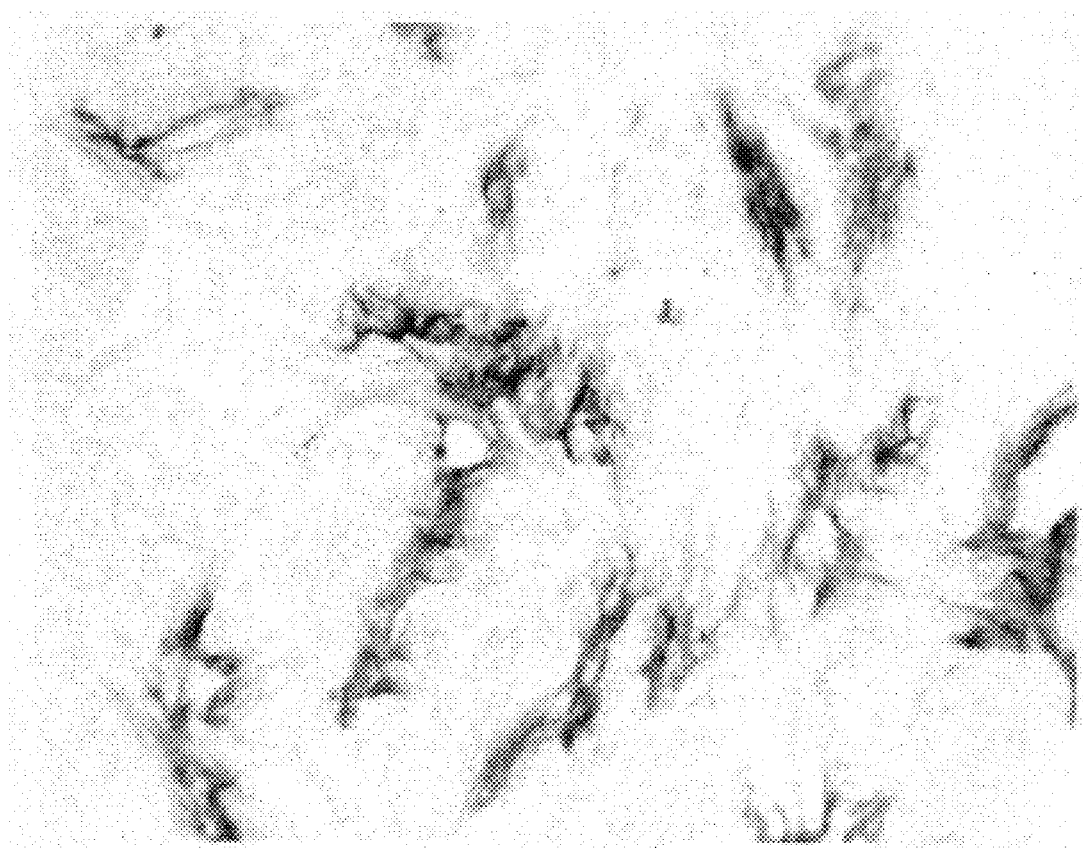
FIG. 4 shows fluorescence microscopy of a U251 glioblastoma tumor section, taken three hours after i.v. injection of Rhodamine-Red-X-labeled TTA1.

Results: TTA1-Red has identical affinity for tenascin-C as the unconjugated parent aptamer, TTA1, at 5 nM. We compared tumor fluorescence levels of TTA1-Red and TTA1.NB-Red 10 min post-injection. The binding aptamer, TTA1-Red, strongly stains the tumor but not adjacent tissue (FIG. 4). In contrast, only tissue auto-fluorescence is detected with TTA1.NB-Red. These results demonstrate the utility of the aptamer in fluorescent detection of tenascin-C in vivo, and the aptamer may be similarly used for staining tissues sections ex vivo.

TABLE 1

Tenascin-C SELEX RNA and protein input.

| Round | Tenascin-C (pMol/well) | RNA (pMol/well) |
|---|---|---|
| 1 | 12 | 200 |
| 2 | 12 | 200 |
| 3 | 12 | 200 |
| 4 | 12 | 200 |
| 5 | 2 | 33 |
| 6 | 2 | 33 |
| 7 | 2 | 33 |
| 8 | 0.2 | 3.3 |

TABLE 2

Cell SELEX/tenascin-C SELEX RNA and protein input

| Round | Tenascin-C (pMol/well) | RNA (pMol/well) |
|---|---|---|
| E9P1 | 2 | 33 |
| E9P2 | 2 | 33 |

TABLE 3

Tenascin-C Sequences: purified protein SELEX (tenascin sequences) and U251 cell SELEX + purified protein SELEX (E9P2 sequences)

Family I

| | | | | | |
|---|---|---|---|---|---|
| TN11 | ggGAggAaCacGcgg | CAAUcAAAACUcACCUUA | UUCCC | UCAUCUAUUAGCUUCCC cagacgacucgcccga | 10 nM |
| TN45 | gggaggacgaugygg | CAAUCUcCGAAAAAGACUCUUCCU | | GCAUCCUCUcACCCCC cagacgacucgcccga | 30 nM |
| TN4 | gggaggacgaugcgg | CAACCUc | GAAAGACUUUUCCC | CCACCACUGUACUCCCC cagacgacuugcccga | 40 nM |
| TN22 | gggaggacgaugcgg | CAACCUC | GAUAGACCCUUCCC | GCAUCACUGUGUACUCCCC cagacgacucgcccga | 40 nM |
| TN32(2) | gggAggAcGauGcgg | cAaCCUcAA | UCUuGaCAUUUCCC | GcACCUAAACUUG CCCC cagacgacucgcccga | 15 nM |
| TN14 | gggaggacgaugcgg | CAAACGAUC | ACU UACCUGCCCU | GCAUCUGCUAGC CUCCCC cagacgacucgcccga | 20 nM |

TABLE 3-continued

Tenascin-C Sequences: purified protein SELEX (tenascin sequences) and U251 cell
SELEX + purified protein SELEX (E9P2 sequences)

| | | | |
|---|---|---|---|
| TN44(3) | gggaggacgaugcgg | ACCCCAGCCAUUCACCCUCGCUUCCACUAUUCCAUCCCCC cagacgacucgcccga | 10 nM |
| TN29(2) | gggaggacgaugcgg | CCAACCUCAUUUUGACACUUCGCCGCACCUAAUUGCCCC cagacgacucgcccga | 25 nM |
| consensus: | | GACNYUUCCN GCAYC | |

Family II

| | | | |
|---|---|---|---|
| E9P2-4(5) | gggaggacgaugcgg | AACCCAUA ACGCGA ACCGACCAACAUGCCUCCCGUGCCCC cagacgacucgcccga | |
| E9P2-1(14) | gggAggaugaugcgg | UGCCCAUAG AAGCAU GCCGCUAAUGCUAACGCCCUCCCC cagacgacucgcccga | 2 nM |
| E9P2-2(16) | gggaggacgaugcgg | UGCCCACU AUGCGU GCCGAAAAACAUUUCCCCCUCUACCC cagacgaucgcccga | 8 nM |
| TN7(3) | gggaggacgaugcgg | AACACUUUCCCAUGCGUCGCC AUCC GGAUAUAUUGCUCC cagacgacucgcccga | 20 nM |
| TN21(4) | gggaggacgaugcgg | ACUGGACCAAACCGUCCCCCAUACCCGGAUACUUUGCUCC cagacgacucgcccga | 10 nM |
| TN9(10) | gggaggacgaugcgg | AACAAUGCACUCGUCGCCGUAAU GGAUGUUUUGCUCCCUG cagacgacucgcccga | 5 nM |
| TN41 | gggaggacgaugcgg | UUAAGUCUCGGUUGAAU GCCCAUCCC AGAUCCCCCUGACC cagacgacucgcccga | 20 nM |
| consensus: | | GCGUCGCCG | |

Orphans

| | | | |
|---|---|---|---|
| E9P2-17 | gggaggacgaugcgg | AUGGCAAGUCCAACCAUCCCCCACGCUUCUCCUGUUCCCC cagacgacucgcccga | |
| E9P2-48 | gggaggacgaugcgg | GAAGUUUUcUCUGCCUUGGUUUCGAUUGGCGCCUccCCCC cagacgacucgcccga | 1 |
| E9P2-14 | gggaggacgaugcgg | UCGAGCCgUCGACCGUCAACAAGAAUAAAGCGUGUCCCUG cagacgacucgcccga | |
| E9P2-17 | gggaggacgaugcgg | AUGGCAAGUCCAACCAUCCCCCACGCUUCUCCUGUUCCCC cagacgacucgcccga | |
| E9P2-22 | gggaggacgaugcgg | ACUACACcgCGAGUCCAUUCAACUUCCCCAAAAaAAAACcUCCCC cagacgacucgcccga | |
| E9P2-40 | gggaggacguagcgg | GAGAUCAACACUCUCUAGUUUGGUUCCAACCUACACCCC cagacgacucgcccga | |
| E9P2-41 | gggaggacgaugcgg | ACGAGCGUCUCAUGAUCACACUAUUUCGUCUCAGUGUGCA cagacgacucgcccga | |
| TN18 | gggaggacgaugcgg | UCGACCUCGAAUGACUCUCCACCUAUCUAACAUCCCCCCC cagacgacucgcccga | 145 nM |
| TN20 | gggaggacgaugcgg | UCGACCUCGAAUGACUCUCCACCUAUCUAACAGCCUUCCC cagacgacucgcccga | |
| TN51 | gggaggacgaugcgg | AGAACUCAUCCUAACCGCUCUAACAAAUCUUGUCCGACCG cagacgacucgcccga | |
| TN8 | gggaggacgaugcgg | AUAAUUcGACCAACCAGGUCCCGGAAAUCAUCCCUCUG cagacgacucgcccga | >10 uM |
| TN27 | gggaggacgaugcgg | AAACCACCGUUGACCAC CUUUUCGUUUCCGAAAGUCCC cagacgacucgcccga | 110 nM |
| TN39 | gggaggacgaugcgg | AAGCCAACCCUCUAGUCAGCCUUUCGUUUCCCACGCCACC cagacgacucgcccga | |
| TN24 | gggaggacgaugcgg | gACCAACUAAACUGUUCGAAAGCUGGAACAUGUCCUGACCC cagacgacucgcccga | 10 nM |
| TN5 | gggaggacgaugcgg | ACCAACUAAACUGUUCGAAAGCUGGAACACGUCCUGACGC cagacgacucgcccga | |
| TN36 | gggaggacgaugcgg | ACCAACUAAACUGUUCGAAAGCUAGAACACGUCCAGACGC cagacgacucgcccga | |
| TN5 | gggaggacgaugcgg | ACCAACUAAACUGUUCGAAAGCUGGAACACGUUCUGACGC cagacgacucgcccga | |
| TN10 | gggaggacgaugcgg | ACCAACUAAACUGUUCGAAAGCUGGAAUACGUCCUGACGC cagacgacucgcccga | |
| TN1 | gggaggacgaugcgg | AAGUUUA GuGCUCCAGUUCCGACACUCCUcUACUCAGCCC cagacgacucgcccga | >10 uM |
| TN109 | gggaggacgaugcgG | AgCCAGAGCCUcUcUcAGUUcUaCAGAACUuACCcACUGG cagacgacucgcccga | |
| TN110 | gggaggacgaugcgg | ACCUAACUCAAUCAGGAACCAAACCUAGCACUCUCAUGCC cagacgacucgcccga | |

U251 SELEX Aptamers, EDTA Elution (E9)

| | | | |
|---|---|---|---|
| E9-8(3) | gggaggacgaugcgg | GAGAUCAACAUUCCUCUAGUUUGGUUCCAACCUACACCCC cagacgacucgcccga | |
| E9-15 | ggcaggacgaugcgg | AUCUCGAUCCUUCAGCACUUCAUUUCAUUCCUUUcUGCCC cagacgacucgcccga | |
| E9-6 | gggaggacgaugcgg | ACCAUCCUUUCCUUAA CAUUUCAUCAUUUCUCUUCUGCCC cagacgacucgcccga | |
| E9-5(2) | gggaggacgaugcgg | UCACGACAACUCGACUG CAUAUCUCAACUCCUGUGCCC cagacgacucgcccga | |
| E9-3(6) | gggaggacgaugcgg | ACUAGACCGCGAGUC CAUUCAACUUGCCCAAAAACCUGCCC cagacgacucgcccga | |
| E9-9 | gggaggacgaugcgg | GCGCAUCGAGCAACAUCCGAUUCGGAUUCCUCCACUCCCC cagacgagu gcccga | |

TABLE 4

2'-OMe Substitutions, Internal Deletions, TTA1, and TTA1.NB

| Sequence | | Kd |
|---|---|---|
| Phase I. 2'-OMe, Affinity. | | |
| TN9.3 | gggaggacgaugcggAACAAUGCACUCGUCGCCCUAAUGGAUGUUUUGCU5 | >10 uM |
| TN9.4 | CCCAGCACGAUGCCCAACAAUGCACUCGUCGCCGUAAUGGAUGUUUGGCUCCCUG5 | 2 nM |
| TN9.4M1 | 66676GACGAUGCGGAACAAUGCACUUGCGCCGUAAUGGAUGUUUUGCUCCCUG5 | 6 nM |
| TN9.4M2 | GGGAG67C67U6C6GAACAAUGCACUCGUCGCCGUAAUGGAUGUUUUGCUCCCUC5 | 20 nM |
| TN9.4M3 | GGGACGACGAUGCG677C77U6C7CUCGUCGCCGUAAUGGAUGUUUUGCUCCCUG5 | 7 nM |
| TN9.4M4 | GGCACCACGAUGCCGAACAAUGCACUC6UC6CC6UAAUCGaUGUUUUGCUCCCUG5 | nb |
| TN9.4M5 | GGCACCACGAUGCGGAACAAUGCACUCGUCGCCCU77U667U6UUUU6CUCCCUC5 | 4 nM |
| TN9.4Me | 6667667C67U6C6677C77U6C7CUCGUCGCC6U77U667U6UUUU6CUCCCU65 | 10 nM |
| Phase III. 2'-OMe, Affinity. | | |
| TN9.4M1235 | 16667667C67U6C6677C77U6C7CUCGUCGCCGU77U667U6UUUU6CUCCCU65 | 16.5 nM |
| TN9.4M135G6 | 1666766ACCAUGCC677C77U6C7CUCCUCGCCGU77U667U6UUUU6CUCCCU65 | 2.2 nM |
| TN9.4M135A7 | 166676G7CGAUGCG677C77U6C7CUCGUCGCCGU77U667U6UUUU6CUCCCU65 | 1.7 nM |
| TN9.4M135G9 | 166676GAC6AUGCG677C77U6C7CUCGUCGCCGU77U667U6UUUU6CUCCCU65 | 7.7 nM |
| TN9.4M135A10 | 166676GACG7UGCG677C77U6C7CUCGUCGCCGU77U667U6UUUU6CUCCCU65 | 1.3 nM |
| TN9.4M135G12G14 | 166676GACGAU6C6677C77U6C7CUCGCCCGU77U667U6UUUU6CUCCCU65 | 2.5 nM |
| TN9.4M135G28 | 166676GACGAUGCG677C77U6C7CUC6UCGCCGU77U667U6UUUU6CUCCCU65 | 37 nM |

TABLE 4-continued

2'-OMe Substitutions, Internal Deletions, TTA1, and TTA1.NB

| Sequence | | Kd |
|---|---|---|
| TN9.4M135G31 | 166676GACGAUGCG677C77U6C7CUCGUC<u>G</u>CCGU77U667U6UUUU6CUCCCU65 | 55 nM |
| TN9.4M135G34 | 166676GACGAUGCG677C77U6C7CUCGUCGCC<u>G</u>U77U667U6UUUU6CUCCCU65 | 7 nM |
| TTA1: | 5'-1G667667CG-(CH$_2$CH$_2$O)$_6$-CGUCGCCGU77U667U6UUUU6CUCCCU65 | 5 nM |
| TTA1.NB: | 5'-1G667667CG-(CH$_2$CH$_2$O)$_6$-CGUCGCCGU77U667U6UUUU6CU5 | >5 uM |

6 = mG; 7 = mA; 5 = 3'—3' Cap, 1 = hexyl amine

TABLE 5

Biodistribution of Tc-99m-TTA1 and -TTA1.NB

| | min | TTA1 | TTA1.NB |
|---|---|---|---|
| tumor | 2 | 4.470 ± 0.410 | 4.510 ± 0.300 |
| | 10 | 5.940 ± 0.590 | 3.020 ± 0.210 |
| | 60 | 2.689 ± 0.310 | 0.147 ± 0.018 |
| | 180 | 1.883 ± 0.100 | 0.043 ± 0.004 |
| | 570 | 1.199 ± 0.066 | 0.018 ± 0.001 |
| | 1020 | 1.150 ± 0.060 | N/A |
| blood | 2 | 18.247 ± 1.138 | 15.013 ± 0.506 |
| | 10 | 2.265 ± 0.245 | 2.047 ± 0.195 |
| | 60 | 0.112 ± 0.003 | 0.102 ± 0.019 |
| | 180 | 0.032 ± 0.001 | 0.034 ± 0.003 |
| | 570 | 0.013 ± 0.001 | 0.011 ± 0.001 |
| | 1020 | 0.006 ± 0.001 | N/A |
| lung | 2 | 8.970 ± 1.210 | 8.130 ± 0.960 |
| | 10 | 2.130 ± 0.080 | 1.940 ± 0.230 |
| | 60 | 0.157 ± 0.011 | 0.120 ± 0.005 |
| | 180 | 0.048 ± 0.006 | 0.041 ± 0.003 |
| | 570 | 0.028 ± 0.006 | 0.017 ± 0.002 |
| | 1020 | 0.007 ± 0.001 | N/A |
| liver | 2 | 9.120 ± 0.530 | 7.900 ± 0.350 |
| | 10 | 12.460 ± 1.250 | 9.100 ± 0.830 |
| | 60 | 1.234 ± 0.091 | 0.423 ± 0.095 |
| | 180 | 0.401 ± 0.084 | 0.211 ± 0.059 |
| | 570 | 0.104 ± 0.017 | 0.058 ± 0.003 |
| | 1020 | 0.075 ± 0.003 | N/A |
| spleen | 2 | 5.100 ± 0.410 | 4.860 ± 0.130 |
| | 10 | 2.460 ± 0.210 | 1.220 ± 0.120 |
| | 60 | 0.643 ± 0.076 | 0.110 ± 0.015 |
| | 180 | 0.198 ± 0.026 | 0.038 ± 0.005 |
| | 570 | 0.062 ± 0.004 | 0.020 ± 0.001 |
| | 1020 | 0.030 ± 0.003 | N/A |
| kidney | 2 | 44.430 ± 4.280 | 54.470 ± 1.210 |
| | 10 | 18.810 ± 0.940 | 14.320 ± 2.080 |
| | 60 | 1.514 ± 0.040 | 0.637 ± 0.111 |
| | 180 | 0.286 ± 0.028 | 0.221 ± 0.021 |
| | 570 | 0.140 ± 0.006 | 0.100 ± 0.013 |
| | 1020 | 0.081 ± 0.005 | N/A |
| sm. int. | 2 | 3.690 ± 0.250 | 3.120 ± 0.100 |
| | 10 | 7.010 ± 0.070 | 6.440 ± 0.250 |
| | 60 | 15.716 ± 2.036 | 14.649 ± 0.532 |
| | 180 | 1.479 ± 0.710 | 1.243 ± 0.405 |
| | 570 | 0.219 ± 0.147 | 0.159 ± 0.067 |
| | 1020 | 0.280 ± 0.243 | N/A |
| lg. int. | 2 | 2.340 ± 0.240 | 2.280 ± 0.180 |
| | 10 | 0.890 ± 0.040 | 0.770 ± 0.070 |
| | 60 | 10.799 ± 5.381 | 21.655 ± 11.676 |
| | 180 | 26.182 ± 7.839 | 18.023 ± 3.485 |
| | 570 | 1.263 ± 0.706 | 0.716 ± 0.179 |
| | 1020 | 0.298 ± 0.167 | N/A |
| muscle | 2 | 1.270 ± 0.130 | 1.490 ± 0.050 |
| | 10 | 0.870 ± 0.090 | 1.840 ± 1.000 |
| | 60 | 0.064 ± 0.003 | 0.050 ± 0.004 |
| | 180 | 0.016 ± 0.002 | 0.011 ± 0.001 |
| | 570 | 0.011 ± 0.002 | 0.007 ± 0.001 |
| | 1020 | 0.003 ± 0.0003 | |

What is claimed is:

1. A complex for use in in vivo diagnostics comprising a tenascin-C nucleic acid ligand and a marker.

2. The complex of claim 1 wherein said tenascin-C nucleic acid ligand is identified by the method comprising:
   a) contacting a candidate mixture of nucleic acids with tenascin-C, wherein nucleic acids having an increased affinity to tenascin-C relative to the candidate mixture may be partitioned from the remainder of the candidate mixture;
   b) partitioning the increased affinity nucleic acids from the remainder of the candidate mixture;
   c) amplifying the increased affinity nucleic acids to yield a mixture of nucleic acids enriched for nucleic acids with relatively higher affinity and specificity for binding to tenascin-C, whereby a nucleic acid ligand of tenascin-C may be identified.

3. The complex of claim 2 wherein said candidate mixture of nucleic acids is comprised of single stranded nucleic acids.

4. The complex of claim 3 wherein said single stranded nucleic acids are ribonucleic acids.

5. The complex of claim 4 wherein said candidate mixture of nucleic acids comprises 2'-F (2'-fluoro) modified ribonucleic acids.

6. The complex of claim 1 wherein said marker is selected from the group consisting of radionuclides, fluorophores, magnetic compounds, and biotin.

7. The complex of claim 6 wherein said radionuclide is selected from the group consisting of technetium-99m (Tc-99m), Re-188, Cu-64, Cu-67, F-18, $^{125}$I, $^{131}$I, $^{32}$P, $^{186}$Re.

8. The complex of claim 7 wherein said marker is technetium-99m.

9. The complex of claim 8 further comprising a linker.

10. The complex of claim 9, wherein said linker has the structure

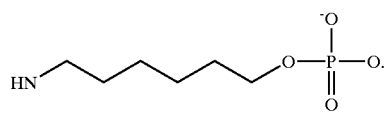

11. The complex of claim 10, wherein said complex is

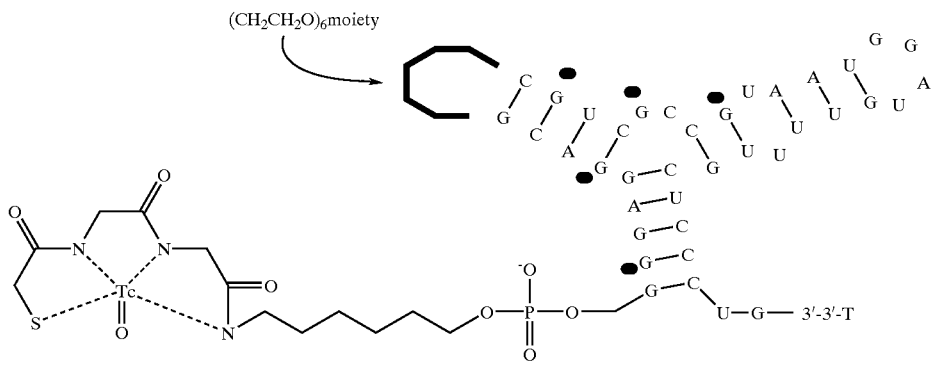

● = 2′-OH G
All A's are 2′OMe modified
All G's, except as indicated, are 2′OMe modified
All C's are 2′F modified
All U's are 2′F modified
(SEQ ID NO:64)

12. A method for the preparation of a complex comprised of a tenascin-C nucleic acid ligand and a marker, said method comprising:
 a) contacting a candidate mixture of nucleic acids with tenascin-C, wherein nucleic acids having an increased affinity to tenascin-C relative to the candidate mixture may be partitioned from the remainder of the candidate mixture;
 b) partitioning the increased affinity nucleic acids from the remainder of the candidate mixture;
 c) amplifying the increased affinity nucleic acids to yield a mixture of nucleic acids enriched for nucleic acids with relatively higher affinity and specificity for binding to tenascin-C to yield a tenascin-C nucleic acid ligand; and
 d) covalently linking said tenascin-C nucleic acid ligand with a marker.

13. The method of claim 12 wherein said marker is selected from the group consisting of radionuclides, fluorophores, magnetic compounds, and biotin.

14. The method of claim 13 wherein said radionuclide is selected from the group consisting of Tc-99m, Re-188, Cu-64, Cu-67, F-18, $^{125}$I, $^{131}$I, $^{32}$P, $^{186}$Re.

15. The method of claim 14 wherein said marker is Tc-99m.

16. The method of claim 15 further comprising a linker.

17. The complex of claim 16, wherein said linker has the structure

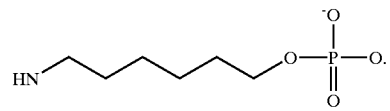

18. The complex of claim 17, wherein said complex is

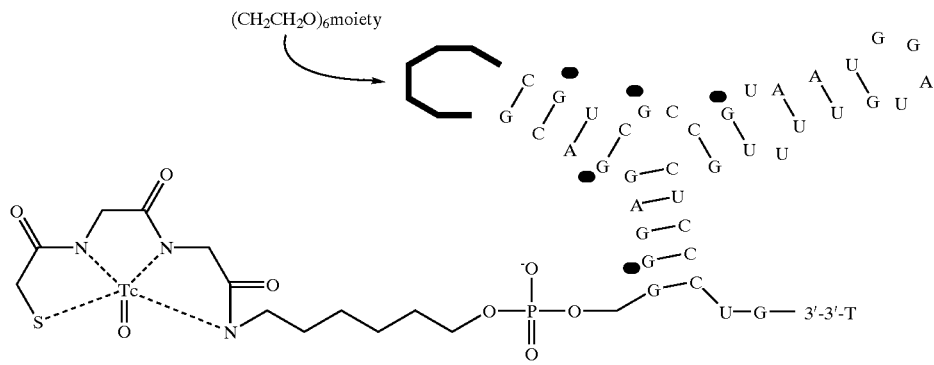

● = 2′-OH G
All A's are 2′OMe modified
All G's, except as indicated, are 2′OMe modified
All C's are 2′F modified
All U's are 2′F modified
(SEQ ID NO:64)

* * * * *